(12) United States Patent
Bernini et al.

(10) Patent No.: US 8,696,617 B2
(45) Date of Patent: Apr. 15, 2014

(54) PORTABLE DRUG ADMINISTRATION DEVICE AND METHOD FOR CONTROLLING A PORTABLE DRUG ADMINISTRATION DEVICE

(75) Inventors: Nicole Bernini, Ersigen (CH); Reto Sigrist, Golaten (CH); Andrea Schutz, Bern (CH)

(73) Assignee: Roche Diagnostics International AG, Rotkreuz (CH)

( * ) Notice: Subject to any disclaimer, the term of this patent is extended or adjusted under 35 U.S.C. 154(b) by 0 days.

(21) Appl. No.: 12/641,500

(22) Filed: Dec. 18, 2009

(65) Prior Publication Data

US 2010/0160855 A1  Jun. 24, 2010

(30) Foreign Application Priority Data

Dec. 19, 2008  (EP) .................................... 08022100

(51) Int. Cl.
*A61M 5/168* (2006.01)
(52) U.S. Cl.
USPC ............................................ 604/67; 604/504
(58) Field of Classification Search
USPC .............. 604/65–67, 504; 600/319, 365, 347; 607/60
See application file for complete search history.

(56) References Cited

U.S. PATENT DOCUMENTS

| 4,731,051 | A | 3/1988 | Fischell | |
|---|---|---|---|---|
| 6,810,290 | B2 * | 10/2004 | Lebel et al. | 607/60 |
| 7,204,823 | B2 | 4/2007 | Estes et al. | |
| 2002/0065454 | A1 * | 5/2002 | Lebel et al. | 600/365 |
| 2003/0055406 | A1 | 3/2003 | Lebel et al. | |
| 2003/0065308 | A1 * | 4/2003 | Lebel et al. | 604/891.1 |
| 2003/0114836 | A1 * | 6/2003 | Estes et al. | 604/890.1 |
| 2003/0160683 | A1 | 8/2003 | Blomquist | |
| 2006/0173406 | A1 * | 8/2006 | Hayes et al. | 604/67 |
| 2007/0093786 | A1 * | 4/2007 | Goldsmith et al. | 604/890.1 |
| 2007/0124002 | A1 * | 5/2007 | Estes et al. | 700/20 |
| 2008/0275384 | A1 * | 11/2008 | Mastrototaro | 604/66 |
| 2008/0300572 | A1 * | 12/2008 | Rankers et al. | 604/504 |

(Continued)

FOREIGN PATENT DOCUMENTS

WO  2007/056592 A2  5/2007

OTHER PUBLICATIONS

European Search Report, Jul. 7, 2009 for Application No./Patent No. 08022100.5-2320, pp. 1-9.

*Primary Examiner* — Quynh-Nhu H Vu
(74) *Attorney, Agent, or Firm* — Dinsmore & Shohl LLP

(57) ABSTRACT

A portable drug administration device includes a pump and a controller configured to control operation of the pump according to a standard administration mode and a suspend mode in which drug administration is temporarily suspended. The device is configured to generate an event trigger on the occurrence of at least one of an error condition and/or the beginning of a maintenance action by the user. The controller is configured to detect the occurrence of the event trigger, and to store, in response to the event trigger, administration data, the administration data comprising all information that characterizes the current administration according at the time of occurrence of the event trigger automatically in a memory and to switch the device from the standard administration mode to the suspend mode. The controller is further configured to detect the occurrence of a restoring trigger and to retrieve, in response to the restoring trigger, the administration data from the memory, to switch the device from the suspend mode to the standard administration mode and to control the pump to resume administration according to the retrieved administration data.

13 Claims, 2 Drawing Sheets

(56) References Cited

U.S. PATENT DOCUMENTS

2009/0005729 A1\* 1/2009 Hendrixson et al. ............ 604/67
2009/0112626 A1\* 4/2009 Talbot et al. ...................... 705/3
2009/0163855 A1\* 6/2009 Shin et al. ....................... 604/66

\* cited by examiner

PORTABLE DRUG ADMINISTRATION DEVICE AND METHOD FOR CONTROLLING A PORTABLE DRUG ADMINISTRATION DEVICE

CROSS-REFERENCE TO RELATED APPLICATIONS

This application claims the benefit of priority under 35 U.S.C. §119 of European Application No. 08022100.5, filed Dec. 19, 2008.

TECHNICAL FIELD

The invention relates to a portable drug administration device and a method for controlling a portable drug administration device.

BACKGROUND

Portable or ambulatory drug administration devices such as infusion pumps are commonly used to deliver liquid medicaments over an extended time period. Those infusion pumps are, among others, used in the therapy of diabetes mellitus by CSII (Continuous Subcutaneous Insulin Infusion). In the following, reference is made to these types of devices without limiting the scope of the invention to this particular application.

Typical insulin pumps can deliver insulin in a substantially continuous way according to a patient-specific basal administration profile which is variable over the time of day. In addition, those pumps can administer drug boli on demand, for example to compensate for carbohydrate intake and/or undesirably raised blood glucose levels. Those drug boli may be administered according to a pulse profile in a short time of typically less than one minute or may be administered according to one or multiple bolus administration profiles over an extended time period, of, e.g., 30 min or one hour. Drug administration according to the basal administration profile and one or multiple bolus administration profiles is superimposed. Some devices allow the user to temporarily modify the administration in order to meet the special requirements which are present, among others, during illnesses or sportive activities.

Known ambulatory infusion pumps can typically be operated in two to three different main operation modes, a run mode, a stop mode in which substantially no drug is administered and sometimes also a suspend mode which is provided for temporarily suspending the drug administration.

Furthermore, the administration device may have one or multiple error modes to which the device is switched upon the occurrence of an error condition, such as a technical device error, or a blockage of the infusion cannula. In prior art devices, those error modes can be considered as stop modes, too.

In each mode only certain commands/orders may be executed and certain actions may be performed, respectively. In the run mode drug is administered as described above. Exchange of a drug cartridge such as an insulin cartridge or exchange of infusion line may only be performed when the operation mode is the stop mode.

Nowadays, whenever the stop mode is activated upon occurrence of an error condition or resulting from a dedicated user action stopping the drug administration, administration of any bolus according to a bolus administration profile as well as any temporary modification of the administration are cancelled. The administration can be resumed only according to a default administration profile when switching from the stop mode back to the run mode. The stop mode may require a dedicated user action/user input for returning to the run mode. The default administration profile is given by the basal administration profile without any temporary modifications.

U.S. Pat. No. 7,204,823 B2 discloses an infusion pump having a suspend function for temporarily suspending medication administration by the infusion pump. The suspend mode has to be specifically selected and activated by the user. When the user resumes administration, he may select which of those administration profiles which where active when suspending administration are to be resumed.

User faults and inappropriate infusion may occur when an administration device is switched from a stop mode to the run mode. In such cases, the user has to memorize and to manually reactivate or reprogram all bolus administration profiles and temporary modifications to the administration which where active when changing into the stop mode. This step is likely to be forgotten in particular if the stop mode has not been selected intentionally by the user but has been activated because of an error condition.

SUMMARY

Such errors as well inappropriate infusion may be preserved by providing a drug administration device that stores the administration state when switching the device from the standard administration mode to a special operation mode and/or a suspend mode and recalls the administration state when switching back to the standard administration mode.

The term 'standard administration mode' defines the operation of the device in a run mode with drug administration being performed according to a basal administration profile and optionally superimposed bolus administration profiles, including an optional temporary modification. The term 'special operation mode' refers to any operation mode different from the standard administration mode as will be described below.

According to an embodiment, a portable drug administration device is provided that comprises a pump and a controller. The controller is configured to control operation of the pump according to a standard administration mode and a special operation mode which differs from the standard administration mode. The controller is further configured to detect the occurrence of an event trigger and to store—in response to an event trigger—administration data indicative of the current administration status in a memory, and to switch the device from the standard administration mode to the special operation mode. The controller is further configured to detect the occurrence of an restoring trigger and to retrieve—in response to a restoring trigger that is generated when being in the special operation mode—the administration data from the memory, to switch the device from the at least one special operation mode back to the standard administration mode and to control the pump to resume administration according to the retrieved administration data. The portable drug administration device may particularly be a portable infusion pump adapted for the administration of a liquid drug, such as insulin, over an extended time period.

The term 'controller' includes the electronic control circuitry which is typical to be present in such devices and may especially comprise one or multiple microcontrollers, memory circuitry, ASICS, as well as general analogue and digital circuitry as generally known in the art.

The administration data comprises all information that characterizes the current administration according to both basal and bolus administration profiles at the time of occurrence of the event trigger. It may in particular comprise the types of administration profiles, in particular the basal administration profile and bolus administration profiles according to which the pump is currently controlled to administer drug. For bolus administration profiles, it advantageously further comprises information with respect to the drug amount that has already been delivered according to that profile and/or that still remains to be delivered. The administration data advantageously further comprise information with respect to a temporary modification of the administration.

The event trigger is a trigger which is generated upon occurrence of a condition requiring special operational conditions as described exemplary below in more detail. An event trigger may be generated by the controller or may be received from an external device as will be described below. Mode switching based on a dedicated user operation may not be considered as event trigger.

Storing of the administration data can take place only as dedicated action which is performed in response to an event trigger. The storing of the administration data can, however, also take place substantially continuously (e.g. every second, minute or similar) with the administration data being "frozen", i.e. not further modified or updated, upon occurrence an event trigger.

In some embodiments, the device is configured to generate an event trigger on the occurrence of at least one of an error condition and/or the beginning of a maintenance action by the user. Error conditions may result from device errors as well as from hazardous operation conditions resulting, e.g., from a blocked infusion cannula, a leakage or an exhausted power cell. Maintenance actions are operation requiring a physiological manipulation of the device such as replacing an empty drug cartridge or exhausted power cell, replacing an infusion line and/or a cannula after some days of usage, or the like. In some cases, a maintenance action is required in order to resolve an error condition, such as a blocked infusion cannula. The beginning of a maintenance action may automatically be detected by the device. For example, the device may detect a removal of a drug cartridge as first step of replacing the cartridge and accordingly generate an event trigger. Alternatively or additionally, the beginning of a maintenance action may be communicated to the device by the user via an advantageously present user interface.

In some embodiments, the device is adapted to generate and/or receive an event trigger on the occurrence of an exceptional physiological condition of a user. In the framework of diabetes therapy, those conditions may a hypoglycaemic or a hyperglycaemic condition of the user. In case of a hypoglycaemic condition, insulin administration is advantageously temporarily suspended in the special operation mode. In case of a hyperglycaemic condition, an insulin administration is advantageously temporarily performed at an increased administration rate and may further be accompanied by an additional bolus administration according to a bolus administration profile.

In embodiments involving a physiological condition of the user as event trigger, the drug administration device advantageously comprises or is operatively culpable to a physiological condition determination unit. The physiological condition determination unit may especially be a continuous glucose sensor and/or strip-based glucose measurement device as known in the art and may be operatively coupled to the administration device via a wired or wireless data interface. Alternatively or additionally, the device may comprise a user interface by which a physiological condition, such as a recently measured blood glucose value, may be manually entered.

In some embodiments, generation of an event trigger based on a physiological parameter is performed by the device. That is, the administration device is configured to evaluate the physiological value as determined by the physiological condition determination unit and to generate an event trigger if the conditions for an exceptional physiological condition are met. Alternatively or, additionally, the physiological condition determination unit is configured to evaluate the physiological value and to generate an event trigger if the corresponding conditions are met.

In some embodiments, the controller is configured such that, in response to a restoring trigger, the controller automatically retrieves the administration data from the memory, switches the device from the special operation mode to the standard administration mode and controls the pump to resume administration according to the retrieved administration data.

A restoring trigger indicates that the device may switch back to the standard administration mode. A restoring trigger is advantageously generated upon error recovery, completion of a maintenance action, and/or cessation of a special physiological condition of the user. A device according to this type of embodiment is especially comfortable to use due to a high level of automation.

In some embodiments, the controller is configured such that, in response to a restoring trigger, the controller waits for a user input to retrieve the administration data from the memory, to switch the device from the special operation mode to the standard administration mode and to control the pump to resume administration according to the retrieved administration data. Alternatively, the controller is configured such that, in response to a restoring trigger, the controller automatically retrieves the administration data from the memory but switches the device back into the standard administration mode and controls the pump to resume administration only on a user input. Even though this type of embodiment requires an additional user input before resuming administration, it may be found to be favourable for safety reasons.

In some embodiments, the controller is configured, in response to a restoring trigger, to selectively resume administration according to a default administration profile. Selection may, for example be based on the time in the special operation mode. After a time of, e.g., 30 min or one hour, continuation of a previously suspended bolus administration as well as any temporary modification of the administration may be disadvantageous and/or even dangerous since the overall conditions may have significantly changed.

In some embodiments, the controller is configured to control the device to switch to a stop mode on the occurrence of a timeout in the special operation mode. Switching from the stop mode to the standard administration mode requires a dedicated user action. When switching back to the standard administration mode, the drug administration is advantageously performed according to a default administration profile. To implement this function, a countdown timer may be provided in the controller which is started when the controller switches the device into the special operations mode.

In some embodiments, the special operation mode comprises at least two special operation modes and the controller is configured to switch the device into either of the at least two special operation modes in dependence of the event trigger. The at least two special operation modes may comprise one or multiple maintenance modes, for example, for replacing an infusion line, a drug cartridge or an exhausted power cell, one or multiple error modes and/or special administration modes for handling exceptional physiological conditions as described above. In some embodiments, the least two special operation modes comprises at least one suspend mode, such that drug administration is temporarily suspended in the special operation mode. Temporarily suspending the drug administration is required for many maintenance actions, such as replacing a drug cartridge.

If the controller is configured to control the device to switch into a stop mode upon occurrence of a timeout in a special operation mode, switching into the stop mode may be performed for some of the at least two special operation modes and to be performed for others. That is, the controller may be configured to selectively control the device to switch into a stop mode upon occurrence on a timeout in a special operation mode or to stay in the special operation mode in dependence of the special operation mode.

In some embodiments, the device comprises a main power cell and a backup power cell and the memory is powered by the backup power cell. This type of embodiment is especially favourable if the main power cell, in particular a battery, may be removed at any time. Further details of this type of embodiment are described in more detail below.

In some embodiments, the controller is configured, in response to a restoring trigger, to calculate the time interval from the occurrence of an preceding event trigger and the restoring trigger, as well as the difference between the actual drug amount delivered within that time interval and a standard drug amount resulting from administration in the standard administration mode within that time interval and to control the pump to compensate for the difference.

The standard drug amount corresponds to the drug amount that would have been delivered in the corresponding time with the device being in the standard administration mode. The actually delivered amount may be smaller, in particular if drug administration was suspended in the special operation mode. It may also be larger, if, for example, drug has been administered at an increased rate in the special operation mode. The controller may be configured to control the pump to compensate for the difference fully or in part.

In another embodiment, a portable drug administration device includes a pump and a controller configured to control operation of the pump according to a standard administration mode and a suspend mode in which drug administration is temporarily suspended. The device is configured to generate an event trigger on the occurrence of at least one of an error condition and/or the beginning of a maintenance action by the user. The controller is configured to detect the occurrence of the event trigger, and to store, in response to the event trigger, administration data, the administration data comprising all information that characterizes the current administration according at the time of occurrence of the event trigger automatically in a memory and to switch the device from the standard administration mode to the suspend mode. The controller is further configured to detect the occurrence of a restoring trigger and to retrieve, in response to the restoring trigger, the administration data from the memory, to switch the device from the suspend mode to the standard administration mode and to control the pump to resume administration according to the retrieved administration data.

The method in accordance with one or more embodiments of the invention for controlling a controlling a portable drug administration device as described above comprises the following steps:

detecting the occurrence of an event trigger automatically storing, in response to an trigger, administration data indicative of a current administration status in a memory and switching the device from a standard administration mode to at least one special operation mode, and retrieving, in response to a restoring trigger, administration data from the memory, and switching the device from the at least one special operation mode to the standard administration mode and resuming administration in accordance with the retrieved administration data.

In some embodiments, the special operation mode comprises at least two special operation modes and the method comprises the step of selecting an appropriate special operation mode from the at least two special operation modes in dependence of the event trigger and switching the device into the selected special operation mode. That is, the special operation mode is selected in dependence of the situation represented by the event trigger.

The at least two special operation modes may comprise one or multiple maintenance modes, for example for replacing a drug, cartridge, an infusion line, a power cell or the like, one or multiple error modes and/or special administration modes as described above resulting from an exceptional physiological condition of the user.

In another embodiment, a method for controlling a portable drug administration device includes detecting the occurrence of an event trigger; automatically storing, in response to an event trigger, administration data indicative of a current administration status in a memory and switching the device from a standard administration mode to a suspend mode; detecting the occurrence of a restoring trigger; and retrieving, in response to the restoring trigger, administration data from the memory, and switching the device from the suspend mode to the standard administration mode and resuming administration in accordance with the retrieved administration data.

Further aspects as well as advantageous embodiments of the method for operating a portable drug administration device may be directly derived from the embodiments of a drug administration device according to the invention as well as the exemplary embodiments described below in more detail.

BRIEF DESCRIPTION OF THE DRAWINGS

In the following, exemplary embodiments of the invention are described in greater detail with reference to the figures.

DETAILED DESCRIPTION

Figure 1:
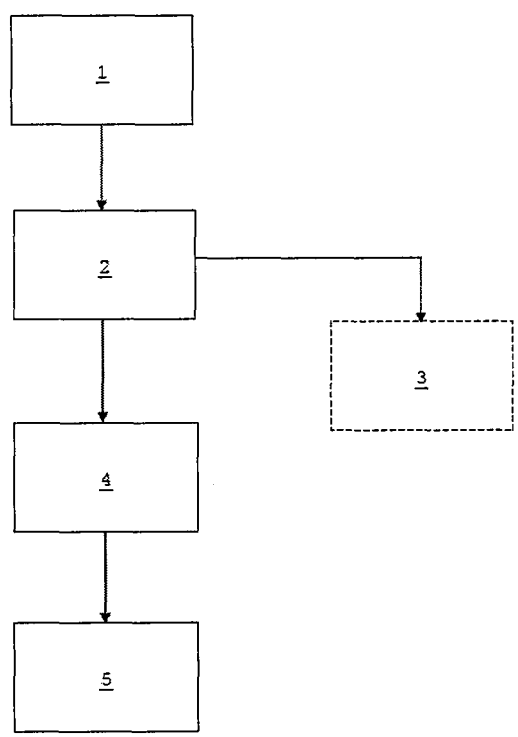
FIG. 1 shows a flowchart of the method according to one or more embodiments the invention.

In FIG. 1, a flowchart of the method of one or more embodiments of the invention is depicted. In a first step 1 the occurrence of an event trigger is detected by the controller of a drug administration device according to one or more embodiments of the invention. This step is repeated continuously or repeatedly as long as the administration device is in the standard administration mode. In the second step 2, the administration data indicative of a current administration state are stored in a memory and the drug administration device is switched by the controller from the standard administration mode to a special operation mode, with the storing of the administration data and the switching to the special operation mode taking place automatically in response to the event trigger. If more than one special operation mode is provided, this step may further comprise the step of selecting an appropriate special operations mode in dependence of the event trigger. Depending on the particular application, the special operation mode can be either of the special operation modes as described above.

Along with switching to the special operation mode, a countdown timer of the controller is started. If the special operation mode is a mode associated with suspending the drug administration and the device has been in that mode for a certain predefined time period without a restoring event being detected, the occurrence of a timeout is established by the countdown timer and the controller switches the drug administration device into a stop mode (step 3 in FIG. 2 with the dashed box representing the step 3 being optional). Monitoring of the occurrence of a timeout by the controller and switching to the stop mode upon occurrence of a timeout is favourable since most of the administration data, such as temporary modifications of the basal admonition and bolus administrations become obsolete after some time in the suspend mode and should therefore not be resumed since the overall situation may have substantially changed.

In step 4, the occurrence of a restoring event is detected by the controller of the drug administration device. The steps of monitoring the occurrence of a timeout and monitoring the occurrence of a restoring event are performed continuously or periodically as long as the administration device is in a special operation mode. In step 5 the administration data is retrieved from the memory, the drug administration device is switched from the special operation mode back to the standard administration mode and drug administration is resumed in accordance with the retrieved administration data. The retrieval of the administration data, the return to the standard administration mode can either take place automatically in response to the restoring event or after the user has been prompted for a user input and the appropriate user input has been provided by the user. The resumed drug administration is performed in accordance with the administration data which where stored in step 2. A compensatory amount of drug may be delivered when administration is resumed in step 5 to compensate for the duration the drug administration was suspended or reduced in the special operation mode.

For the drug administration device being an insulin pump, the event trigger may for example be generated upon the detection of an error such as a blockage of the infusion cannula or a power cell (e.g. a battery) of the insulin pump being empty, a (non-empty) power cell (e.g. a battery) of the insulin pump being temporarily removed, or of the insulin cartridge of the insulin pump being substantially empty. The event trigger may also be generated upon the beginning of a maintenance action which is performed by a user and detected by the controller of the insulin pump, such as the removal of the insulin cartridge by the user.

If the drug administration device is given by an insulin pump, the restoring trigger may be the recovery of the error detected by the controller or the completion of a maintenance action such as removal of a detected occlusion, insertion of a charged power cell, re-insertion of a (non-empty) power cell that had been temporarily removed, or insertion of a filled insulin cartridge. Detection of such events indicates that the infusion pump is able to deliver insulin again and insulin administration is resumed in accordance to the retrieved administration data. Further examples of the second event are conceivable.

For example, if the user removes the power cell of the insulin pump because it is empty, this constitutes an event trigger which is detected by the controller (confer step 1 of FIG. 1). The controller then stores the administration data indicative of the current administration status, switches the infusion pump to the corresponding special operation mode and may inform the user about the switch to the special operation mode by means of a corresponding acoustic, tactile (e.g. a vibratory) or optical signal (confer step 2 of FIG. 1).

Informing the user about the emptiness (or removal, respectively) of the power cell increases the safety of the user. When the user reinserts a new or recharged power cell this is detected by the controller as second event (confer step 4 of FIG. 1). The infusion pump is then either automatically switched back into the standard administration mode with insulin administration being resumed according to the retrieved administration data or the user is prompted via the user interface of the insulin pump and/or a remote user interface to indicate if he wants to resume insulin administration (confer step 5 of FIG. 1). If the user does not give an input if prompted or if he gives an input indicating that he does not want to resume administration then the infusion pump either remains in the current special operation mode or is switched to the stop mode. When or before administration according to the standard administration mode is resumed, the relevant administration data according to which administration is to be resumed are displayed or indicated. In a further option, the user may decide not to resume administration according to all administration data but to selectively resume administration. For example, he may decide to cancel a temporary modification of the basal administration but resume the administration of a bolus.

In this example, the insulin pump may comprise a backup power cell for supplying the device with the main power cell being empty or removed.

If, according to another example, the user removes the insulin cartridge from the insulin pump, this constitutes an event trigger which is detected by the controller (confer step 1 of FIG. 1). The controller then stores the administration data indicative of the current administration status, switches the infusion pump to a corresponding maintenance mode and may depict the corresponding menus and/or submenus on a display of the user interface of the insulin pump to guide the user through the procedure of cartridge replacement (confer step 2 of FIG. 1). When the user has inserted a new, filled cartridge into the corresponding cartridge compartment of the insulin pump and the tube-filling process has been completed or accepted by the user as completed, this is detected by the controller as restoring event (confer step 4 of FIG. 1), the insulin pump being now ready to restart insulin administration. The infusion pump is then either automatically switched back into the standard administration mode with insulin administration being resumed according to the retrieved administration data or the user is prompted via the user interface of the insulin pump to indicate if he wants to resume insulin administration (confer step 5 of FIG. 1). If the user indicates by a corresponding user input that insulin administration shall be resumed, then the infusion pump is switched back into the standard administration mode with insulin administration being resumed according to the retrieved administration data (confer step 5 of FIG. 1). If the user does not give an input if prompted or if he gives an input indicating that he does not want to resume administration then the infusion pump either remains in the suspend mode or is switched to the stop mode.

The event trigger may also be generated upon the occurrence of a exceptional physiological condition of the user, for example that a current glucose measurement of a glucose sensor reaches or falls below a predefined hypoglycaemia threshold or reaches or exceeds a predefined hyperglycaemic threshold. Alternatively or additionally to the glucose sensor, a strip-based glucose measurement device may be used for determining the glucose measurement. Such a strip-based glucose measurement device typically performs single measurements on demand. Each measurement value is transferred from the strip-based glucose measurement device to the drug administration device via a data interface or by a manual user input. The glucose sensor along with the corresponding measurement and evaluation circuitry or the strip-based glucose measurement device are exemplary physiological condition determination units.

The restoring event may then be given by a cessation of this exceptional physiological condition of the user that is detected by the controller, for example that a current glucose measurement of a glucose sensor now surpasses/lies above the predefined hypoglycaemia threshold.

If a strip-based glucose measurement device is used instead of a glucose sensor, then the restoring event may be given be a triggering signal generated by a time trigger a certain period (e.g. several hours) after the occurrence of the first event, by a manual user action/input or by a further glucose measurement taken by the strip-based glucose measurement device. The special operation mode may—depending on the particular application—be a suspend mode, in which temporarily no insulin administration takes place, or another special operation in which only a reduced insulin amount is administered.

Figure 2:
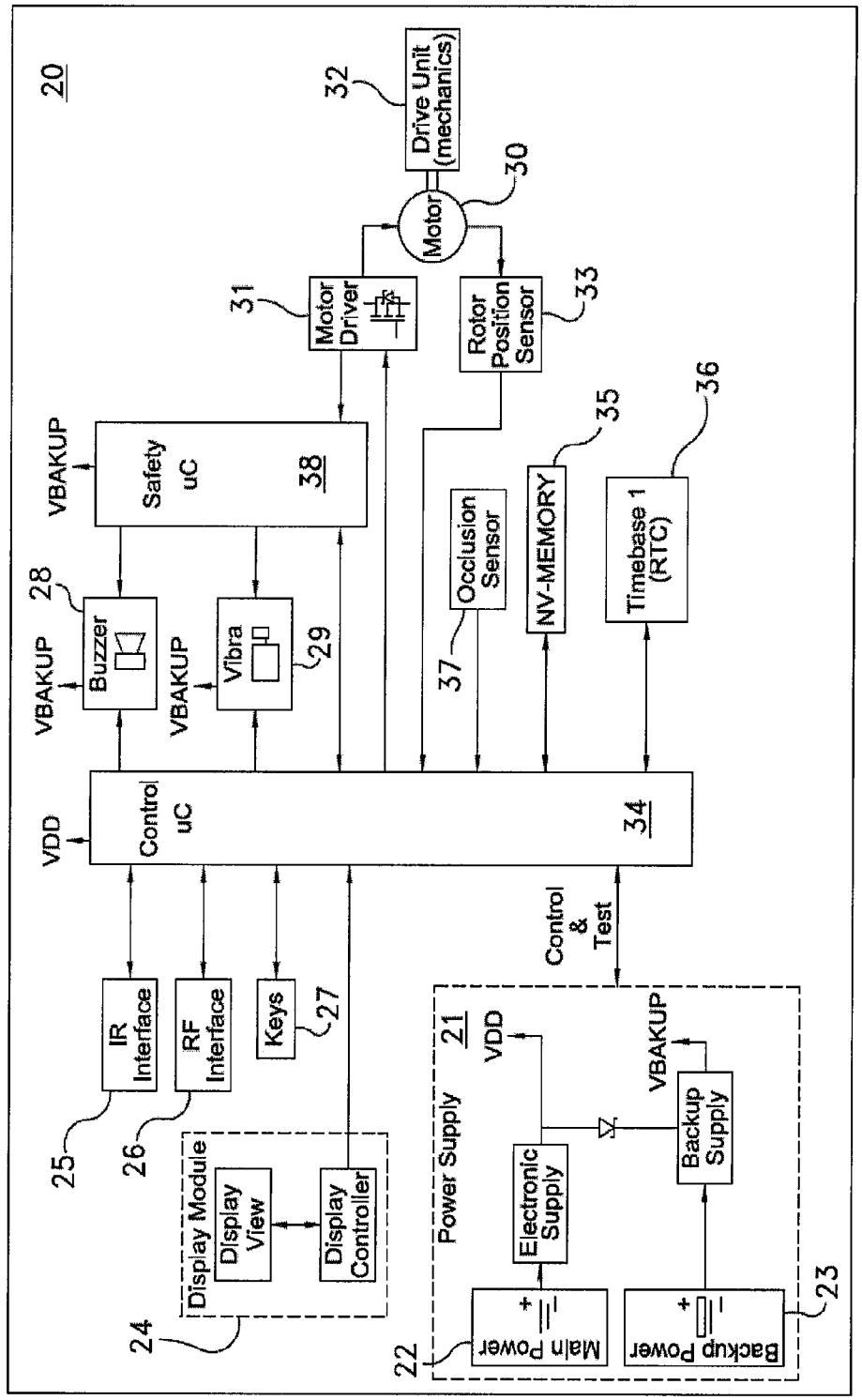
FIG. 2 shows a block diagram of a drug administration device according to one or more embodiments of the invention in form of an infusion pump.

FIG. 2 shows a block diagram of a drug administration device according to one or more embodiments of the invention in form of an insulin pump 20. The insulin pump 20 comprises a power supply 21 that is configured redundantly with two power cells 22, 23, one being a main power cell 22 and one being a backup power cell 23. The backup power cell 23 is not removable (and advantageously not replaceable) in contrast to the main power cell 22. The backup power cell 23 is charged by the main power cell 22 during normal operation. Besides being a rechargeable battery, the backup power cell 23 may be a high capacity condenser or the like. The insulin pump 20 further comprises a user interface with a display module 24, an infrared (IR) interface 25, a radio frequency (RF) interface 26 and keys 27 (e.g. of a keypad) for user inputs. For generation of a tactile signal in form of a vibratory signal and for generation of an acoustic signal, for example for informing or warning the user, a buzzer 28 and a vibrator 29 are provided. An electric motor 30 with a motor driver 31 are provided for driving a piston rod (not shown) to controllably displace the insulin out of the cartridge and its associated infusion line and infusion cannula into the body of the user. The motor 30 is provided with a rotor position sensor 33.

A controller 34 in form of a microcontroller is provided for controlling the power supply 21, the display module 24, the buzzer 28, the vibrator 29, the motor driver 31 and a memory 35. Associated with the controller 34 is a real time clock (RTC) 36. The user inputs via the keys 27, the measurement signals of the rotor position sensor 33 and the measurement signals of an occlusion sensor 37 constitute inputs to the controller 34 among others.

The controller 34 is powered by the main power cell 22 in this exemplary embodiment, but may also be powered by the (non-removable) backup power cell 23. Powering the controller 34 by the non-removable backup power cell 23 is particularly advantageous if administration data are stored only in response to an event trigger rather than being stored substantially continuously and being "frozen" upon occurrence of an event trigger. Then the controller 34 can still detect a removal of the main power cell 22 or any other sort of breakdown or failure of the main power cell 22 (generating an event trigger) and is still operable to store the administration data and to switch to the special operation mode in response to this event trigger.

In the embodiment shown in FIG. 2, the controller 34 is configured such that it stores the administration data representing the current administration status substantially continuously in the memory 35. In response to an event trigger which may be, for example, the detection of an occlusion by the occlusion sensor 37, the administration data in the memory 35 are not further updated and the insulin pump 20 is switched from the standard administration mode to an special operation mode as described above. In the example of an occlusion, the corresponding special operation mode may be an error mode in which the error is indicated and drug administration is suspended. The controller 34 is further configured such that, in response to a restoring trigger (given e.g., by the steps for replacing an occluded infusion cannula), the administration data is retrieved from the memory 35, the insulin pump 20 is switched from the special operation mode, e.g. the error mode, to the standard administration mode and insulin administration is resumed in accordance with the retrieved administration data as described above. Furthermore, a safety unit 38 is provided which is realized by a microcontroller and communicates with the controller 34. The safety unit 38 in particular monitors the insulin administration and triggers the buzzer 28 and/or the vibrator 29 if an error occurs to alarm the user. The controller 34 may also be given by a set of two or more separate controllers for safety and redundancy reasons, wherein for example one controller is primarily responsible for controlling the insulin administration and one controller is primarily responsible for controlling the user interface, the power supply and connectivity.

All documents cited herein are incorporated herein by reference; the citation of any document is not to be construed as an admission that it is prior art with respect to the present invention.

It is to be understood that while certain embodiments of the present invention have been illustrated and described herein, it is not to be limited to the specific embodiments described and shown.

What is claimed is:

1. A portable drug administration device for a user comprising:
 a pump;
 a controller configured to control operation of the pump according to a standard administration mode and a suspend mode in which drug administration is temporarily suspended; wherein
 the device is configured to generate an event trigger based on the occurrence of an error condition of the drug administration device or a beginning of a maintenance action on the device by the user, the error condition including at least one of a device error, a blocked infusion cannula, a leakage, and an exhausted power cell;
 the controller is configured to detect the occurrence of the event trigger, and to store, in response to the event trigger, administration data, the administration data comprising all information that characterizes the current administration at the time of occurrence of the event trigger automatically in a memory and to automatically switch the device from the standard administration mode to the suspend mode; and
 the controller is further configured to detect the occurrence of a restoring trigger generated upon recovery from the error condition or completion of the maintenance action, and to retrieve, in response to the restoring trigger, the administration data from the memory, and to automatically switch the device from the suspend mode to the standard administration mode and to control the pump to resume administration according to the retrieved administration data.

2. The drug administration device according to claim 1, wherein the controller is configured such that, in response to the restoring trigger, the controller automatically retrieves the administration data from the memory, switches from the suspend mode to the standard administration mode and controls the pump to resume administration according to the retrieved administration data.

3. The drug administration device according to claim 1, wherein the controller is configured such that, in response to the restoring trigger, the controller waits for a user input to retrieve the administration data from the memory, switches the device from the suspend mode to the standard administration mode and controls the pump to resume administration according to the retrieved administration data.

4. The drug administration device according to claim 1, wherein the controller is configured, in response to the restoring trigger, to selectively control the pump to resume administration according to a default administration profile selected based on the period of time the device was in suspend mode.

5. The drug administration device according to claim 1, wherein the controller is configured to control the device to switch to a stop mode on the occurrence of a timeout in the suspend mode.

6. The drug administration device according to claim 1, wherein the device is further configured to generate, to receive, or to generate and receive an event trigger on the occurrence of a special physiological condition of the user.

7. The drug administration device according to claim 6, wherein the device comprises or is operatively culpable to a physiological condition determination unit and the device, the physiological condition determination unit, or the device and the physiological condition determination unit is configured to generate an event trigger based on evaluation of a physiological value determined by the physiological value evaluation unit.

8. The drug administration device according to claim 6, wherein the exceptional physiological condition comprises at least one of the occurrence of a hypoglycaemic or a hyperglycaemic condition of the user.

9. The drug administration device according to claim 1, wherein the device comprises a main power cell and a backup power cell and the memory is powered by the backup power cell.

10. The drug administration device according to claim 1, wherein the suspend mode is one of at least two special operation modes and the controller is configured to switch into either of the at least two special operation modes in dependence of the event trigger.

11. The drug administration device according to claim 1, wherein the controller is configured, in response to the restoring trigger, to calculate the time interval from the occurrence of a preceding event trigger and the restoring trigger, as well as the difference between the actual drug amount delivered within that time interval and a standard drug amount resulting from administration in the standard administration mode within that time interval and to control the pump to compensate for the difference.

12. A method for controlling a portable drug administration device used with a user, comprising:
    detecting an event trigger resulting from the occurrence of an error condition of the drug administration device or a beginning of a maintenance action on the device by the user, the error condition including at least one of a device error, a blocked infusion cannula, a leakage, and an exhausted power cell;
    automatically storing, in response to an event trigger, administration data indicative of a current administration status in a memory and automatically switching the device from a standard administration mode to a suspend mode;
    detecting the occurrence of a restoring trigger generated upon recovery from the error condition or completion of the maintenance action; and
    retrieving, in response to the restoring trigger, administration data from the memory, and automatically switching the device from the suspend mode to the standard administration mode and resuming administration in accordance with the retrieved administration data.

13. The method according to claim 12, wherein the suspend mode is one of at least two special operation modes and the method comprises the step of selecting an appropriate special operation mode from the at least two special operation modes in dependence of the event trigger and switching the device into the selected special operation mode.

* * * * *

UNITED STATES PATENT AND TRADEMARK OFFICE
CERTIFICATE OF CORRECTION

Page 1 of 1

PATENT NO. : 8,696,617 B2
APPLICATION NO. : 12/641500
DATED : April 15, 2014
INVENTOR(S) : Nicole Bernini, Reto Sigrist and Andrea Schutz It is certified that error appears in the above-identified patent and that said Letters Patent is hereby corrected as shown below:

In the Specification,

Col. No. 5, Line No. 49, "according at the time" should read --accordingly at the time--;

Col. No. 5, Line No. 59, "for controlling a controlling a portable" should read --for controlling a portable drug--;

Col. No. 6, Line No. 43, "more embodiments the invention" should read --more embodiments of the invention--;

Col. No. 7, Line No. 32, "administration data which where stored" should read --administration data which were stored--;

Col. No. 9, Line No. 12, "may be given be" should read --may be given by--; and

Col. No. 9, Line No. 13, "generated by a time trigger a certain" should read --generated by a time trigger for a certain--.

Signed and Sealed this
Thirtieth Day of December, 2014

Michelle K. Lee
*Deputy Director of the United States Patent and Trademark Office*